United States Patent
Loughman et al.

(10) Patent No.: US 12,263,241 B1
(45) Date of Patent: Apr. 1, 2025

(54) CANNABIS COMPOSITIONS, ORAL PRODUCTS, AND METHODS OF MAKING SAME

(71) Applicant: J.D.I.P., LLC, Palisade, CO (US)

(72) Inventors: Jesse Loughman, Palisade, CO (US); Tyler Hutchinson, Palisade, CO (US)

(73) Assignee: J.D.I.P., LLC, Palisade, CO (US)

( * ) Notice: Subject to any disclaimer, the term of this patent is extended or adjusted under 35 U.S.C. 154(b) by 0 days.

(21) Appl. No.: 18/664,248

(22) Filed: May 14, 2024

Related U.S. Application Data

(60) Provisional application No. 63/603,072, filed on Nov. 27, 2023.

(51) Int. Cl.
| | | |
|---|---|---|
| A61K 9/00 | (2006.01) |
| A61K 31/00 | (2006.01) |
| A61K 47/02 | (2006.01) |
| A61K 47/26 | (2006.01) |
| A61K 47/38 | (2006.01) |
| A61K 47/46 | (2006.01) |

(52) U.S. Cl.
CPC .......... *A61K 9/0056* (2013.01); *A61K 31/658* (2023.05); *A61K 47/02* (2013.01); *A61K 47/26* (2013.01); *A61K 47/38* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 10,933,016 B2 | 3/2021 | Mandel et al. |
| 11,166,935 B2 | 11/2021 | Bruun |
| 11,534,413 B2 | 12/2022 | Mandel |
| 11,534,421 B2 | 12/2022 | Bruun |
| 2012/0231083 A1* | 9/2012 | Carley | A61K 9/146 424/490 |
| 2019/0015383 A1* | 1/2019 | Woelfel | A61K 9/1075 |
| 2019/0060225 A1 | 2/2019 | Mandel et al. |
| 2019/0201372 A1* | 7/2019 | Mckay | A61K 9/1271 |
| 2019/0254326 A1* | 8/2019 | Welsh | A23P 10/40 |
| 2020/0179329 A1 | 6/2020 | Bruun |
| 2021/0077389 A1 | 3/2021 | Mandel et al. |
| 2021/0177037 A1 | 6/2021 | Gerardi et al. |
| 2021/0177043 A1 | 6/2021 | Gerardi et al. |
| 2021/0177044 A1 | 6/2021 | Gerardi et al. |
| 2021/0177739 A1 | 6/2021 | Gerardi et al. |
| 2021/0186081 A1 | 6/2021 | Gerardi et al. |
| 2021/0330590 A1 | 10/2021 | Hutchens et al. |
| 2021/0338629 A1 | 11/2021 | Garabagi et al. |
| 2023/0225965 A1 | 7/2023 | Tir et al. |

FOREIGN PATENT DOCUMENTS

| | | | | |
|---|---|---|---|---|
| AU | 2003227735 A1 * | 12/2003 | | A61K 36/60 |
| WO | 2016/094810 A2 | 6/2016 |
| WO | 2021/116825 A1 | 6/2021 |
| WO | 2022/119840 A1 | 6/2022 |
| WO | 2022/219063 A1 | 10/2022 |
| WO | 2022/241420 A1 | 11/2022 |

OTHER PUBLICATIONS

"International Search Report and Written Opinion of the International Searching Authority," issued in connection with Int'l Appl. No. PCT/US2024/029339, dated Sep. 9, 2024 (10 pages).

\* cited by examiner

*Primary Examiner* — Melissa S Mercier
(74) *Attorney, Agent, or Firm* — Holland & Hart LLP

(57) ABSTRACT

The disclosed technology includes cannabinoid oral products, and methods for making same. In some embodiments, the oral products are pouches including cannabinoid infused wafers. In some embodiments, the method of making the cannabinoid oral products includes preparing an emulsion, preparing a spray dry solution, spray drying solution into cannabinoid and carbohydrate particles, preparing a paste, preparing a wafer in a heated vacuum oven, fragmenting the wafer into cannabinoid infused wafer fragments, mixing the cannabinoid infused wafer fragments with starch, and dispensing the cannabinoid infused wafer fragments into pouches. The methods may also include labeling the oral products, for example, with a THC warning symbol.

11 Claims, 3 Drawing Sheets

```
┌─────────────────────────────┐
│      Prepare emulsion       │─── 102
└──────────────┬──────────────┘
               ▼
┌─────────────────────────────┐
│   Prepare spray dry solution │─── 104
└──────────────┬──────────────┘
               ▼
┌─────────────────────────────┐
│ Spray dry solution into particles │─── 106
└──────────────┬──────────────┘
               ▼
┌─────────────────────────────┐
│        Prepare paste        │─── 108
└──────────────┬──────────────┘
               ▼
┌─────────────────────────────┐
│ Prepare wafer in a heat vacuum │─── 110
└─────────────────────────────┘
```

CANNABIS COMPOSITIONS, ORAL PRODUCTS, AND METHODS OF MAKING SAME

CROSS REFERENCE TO RELATED APPLICATIONS

This claims priority to and the benefit of U.S. Provisional Patent Application No. 63/603,072, entitled "*Cannabis* COMPOSITIONS, POUCHES, AND METHODS OF MAKING SAME," filed Nov. 27, 2023, the disclosure of which is hereby incorporated by reference in its entirety.

BACKGROUND OF CERTAIN ASPECTS OF THE DISCLOSURE

Consumers who desire *Cannabis* products may not want to engage in smoking or vaping. To avoid stigma or side effects (e.g., rapid absorption into the blood via the lung) associated with smoking or vaping, consumers may seek alternative methods of administration. *Cannabis* dips or chews are an available method of marijuana use where a user places the dip or chew between the gums and cheek for a period of time. However, there are drawbacks to chewing the *Cannabis* flower. *Cannabis* dips can have a bad taste, be ineffective, and have harmful microorganisms. While some dips or chews may be made by complex manufacturing processes with *Cannabis* extracts and coco coir or other plant fibers to avoid these drawbacks, consumers may not want to emulate the look and feel of chewing tobacco. Accordingly, it is desirable for consumers to have a discreet, manageable method of administration of *Cannabis* at an absorption rate slower than smoking or vaping.

BRIEF SUMMARY OF SOME ASPECTS OF THE DISCLOSURE

The disclosed technology includes cannabinoid compositions, pouches, and methods for making same. In some embodiments, the methods include making cannabinoid infused wafers. In some embodiments, the cannabinoid compositions, pouches, and wafers include cannabinoid infused wafer fragments. In some embodiments, liposomal and/or micellar cannabinoid nanoparticles are used to form the wafer.

In some embodiments, the methods include making a wafer, including preparing an emulsion, preparing a spray dry solution, spray drying the solution into particles, preparing a paste with the particles, and preparing a dry wafer in a heated vacuum oven.

In some embodiments, the methods include making cannabinoid pouches, including preparing an emulsion, preparing a spray dry solution, spray drying the solution into cannabinoid and carbohydrate particles, preparing a paste with the cannabinoid and carbohydrate particles, preparing a wafer in a heated vacuum oven, fragmenting the wafer into cannabinoid infused wafer fragments, coating the cannabinoid infused wafer fragments, and dispensing the coated cannabinoid infused wafer fragments into pouches. In some embodiments, the cannabinoid infused wafer fragments are coated or mixed with starch. The method may also include labeling the pouches, for example, with a THC warning symbol.

In some embodiments, the methods include coating cannabinoid infused wafer fragments, and dispensing the coated cannabinoid infused wafer fragments into pouches. In some embodiments, the cannabinoid infused wafer fragments are coated or mixed with starch. The method may also include labeling the pouches, for example, with a THC warning symbol.

There are other novel aspects and features of this disclosure. They will become apparent as this specification proceeds. Accordingly, this brief summary is provided to introduce a selection of concepts in a simplified form that are further described below in the detailed description. The summary and the background are not intended to identify key concepts or essential aspects of the disclosed subject matter, nor should they be used to constrict or limit the scope of the claims. For example, the scope of the claims should not be limited based on whether the recited subject matter includes any or all aspects noted in the summary and/or addresses any of the issues noted in the background.

BRIEF DESCRIPTION OF DRAWINGS

The preferred and other embodiments are disclosed in association with the accompanying drawings in which:

FIG. 1 illustrates a flowchart for a method of making a wafer in accordance with aspects of the present disclosure.

DETAILED DESCRIPTION

Figure 2:
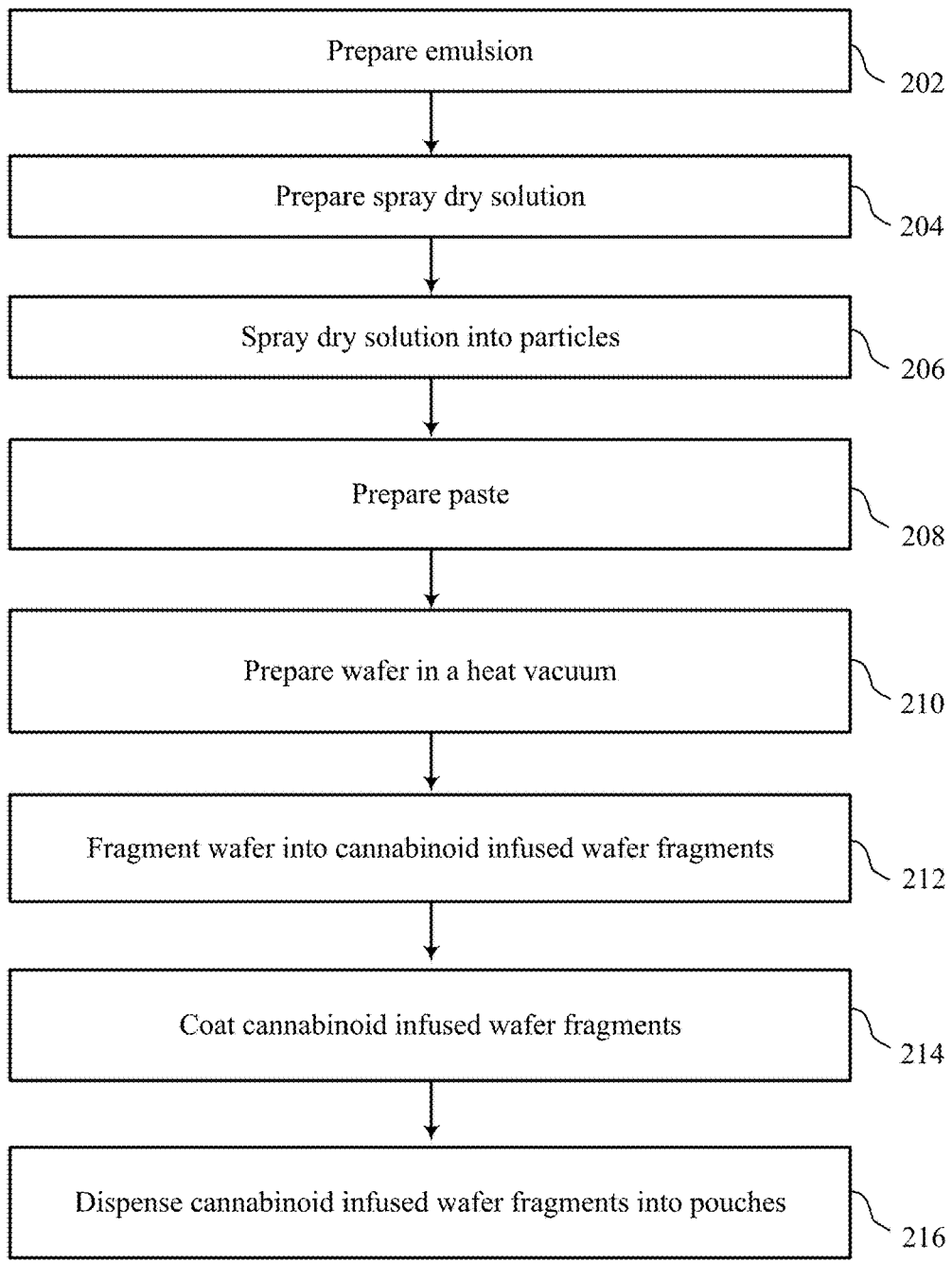
FIG. 2 illustrates a flowchart for a method of making a *Cannabis* pouch in accordance with aspects of the present disclosure.

Cannabinoids, which interact with the body's endocannabinoid system, may be administered for therapeutic benefits without psychoactive properties and/or for intoxicating effects of *Cannabis*. *Cannabis* oral products, including pouches, dips, or chews, are desirable because these products are odorless and a safer alternative to smokable products. No harsh chemicals are inhaled into the lungs with pouches, and they have a slower, longer-lasting high compared to smoking. Similar to other marijuana products, pouches can also be used as a medicament (e.g., pain relief, control nausea and vomiting, increase appetite, lower pressure inside the eyes, etc.) to relieve symptoms of certain conditions, diseases or disorders (e.g., cancer, HIV/AIDS, severe chronic pain, extreme weight loss, multiple sclerosis, Crohn disease, inflammatory bowel disease, epilepsy, glaucoma, etc.).

The disclosed technology includes cannabinoid compositions, oral products, and methods for making same. In some embodiments, the methods include making cannabinoid infused wafers. In some embodiments, the cannabinoid infused wafers may be fragmented into cannabinoid infused wafer fragments. Fragment may include to fragment, break, or otherwise separate into pieces or fragments.

In some embodiments, the oral product is a packet or pouch for oral administration for absorption in the stomach and includes one or more cannabinoids as an active ingredient. The pouch includes a sealed membrane defining an interior area. In some embodiments, the pouch may be a water-permeable pouch or bag. In some embodiments, when the pouch is administered into a user's oral cavity (e.g., between the inner lips and gum, under the tongue, between the cheek and gums), saliva enters the interior area through the membrane. The cannabinoid compositions (including one or more cannabinoids) are dissolved by the saliva. In some embodiments, the cannabinoid composition travels to the stomach of a user and is absorbed primarily by the microvilli of the epithelial lining of the stomach. Residual composition may be absorbed by the small intestine. In some embodiments, the cannabinoids may be dissolved in a prolonged release.

In some embodiments, the pouch is administered for approximately 10-60 minutes. In some examples, the pouch is in a user's mouth for 15-45 minutes. The pouch may be removed from the mouth for disposal. In other embodiments, the infused wafer fragments and the pouch itself may be dissolvable.

In some embodiments, the method of making the cannabinoid pouches includes preparing an emulsion, preparing a spray dry solution, spray drying the solution into a cannabinoid and carbohydrate particles, preparing a paste with the cannabinoid and carbohydrate particles, preparing a wafer in a heated vacuum oven, fragmenting the wafer into cannabinoid infused wafer fragments, coating the cannabinoid infused wafer fragments, and dispensing the cannabinoid infused wafer fragments into pouches. In some embodiments, the cannabinoid infused wafer fragments are mixed or coated with starch. The method may also include labeling the pouches, for example, with a THC warning symbol, for safety and identification purposes, and/or for product branding.

In some embodiments, the method of making a wafer and method of making a pouch does not include cannabinoids. An emulsion may be made with other non-cannabinoid substances, components or compositions. For example, an emulsion may be made with one of pharmaceutical substances or ingredients, food additives, dietary supplements, vitamins, botanical ingredients, stimulants, amino acids, antioxidants, terpenes, and nicotine. Other ingredients are contemplated for making a wafer, and in some embodiments, making wafer fragments and/or incorporating the wafer fragments into oral products.

In some embodiments, the method of making a pouch includes labeling the pouches, for example, with a THC or pharmaceutical warning symbol, for safety and identification purposes, and/or for product branding.

In some embodiments, the disclosed methods include preparation of a dry wafer in a heated vacuum oven containing cannabinoid nanoparticles (e.g., sizes ranging from approximately 100 to 300 nanometers) that can be further made into a dry cannabinoid infused wafer fragments that is easily dispensable into pouches.

In some embodiments, liposomal cannabinoid nanoparticles are used to form the wafer. In some embodiments, micellar cannabinoid nanoparticles are used to form the wafer. In some embodiments, a combination of liposomal and micellar cannabinoid nanoparticles are used to form a wafer.

In some embodiments, in order to create desirable cannabinoid infused wafer fragments to dispense into a pouch, a cannabinoid wafer is created by mixing ingredients and placing the ingredients into a heated vacuum oven to form a wafer. The wafer is then made into cannabinoid infused wafer fragments and dispensed into a pouch. In some embodiments, the pouches have a THC warning sign printed onto each pouch.

In some embodiments, the cannabinoid composition or cannabinoid infused wafer fragments composition comprises a cannabinoid extract or oil extracted from source material includes at least one of cannabidiol, cannabinol, cannabigerol, cannabichromene, cannabidivarol, tetrahydrocannabidiol, tetrahydrocannabigerol, tetrahydrocannabichromene, and tetrahydrocannabidivarol.

In some embodiments, the cannabinoid composition or cannabinoid infused wafer fragments composition comprises at least one of carbohydrates, sugars, sugar alcohol, maltodextrin, sucralose, modified food starches, cornstarch, microcrystalline cellulose, THC distillate, MCT oil, baking soda, natural flavoring, botanical terpenes, vanilla extract, and salt. In some embodiments, the cannabinoid composition or cannabinoid infused wafer fragments composition do not comprise of microcrystalline cellulose.

In some embodiments, the cannabinoid composition or cannabinoid infused wafer fragments composition is a "wafer-derived" cannabinoid composition including cannabinoid nano emulsions. The term "wafer-derived" refers to preparation of a wafer in a heated vacuum oven containing cannabinoids (e.g., cannabinoid nano emulsions) into a dry cannabinoid infused wafer fragments to dispense into pouches.

In some embodiments, the pouch includes cannabinoid infused wafer fragments include approximately 0.5-4% by weight of water-soluble encapsulated cannabinoid nanodroplets. In some embodiments, the water-soluble encapsulated cannabinoid nanodroplets are approximately 100 nm-300 nm.

In some embodiments, the pouch includes cannabinoid infused wafer fragments include a water insoluble composition containing approximately 8-29% microcrystalline cellulose and cellulose fibers.

In some embodiments, the pouch is at least one of flavored, sugarless, and vegan-friendly.

In some embodiments, the pouch includes microcrystalline cellulose powder. In some embodiments, the pouch includes cellulose and thermoplastic fibers, and propylparaben. Referring to FIG. 1, a flowchart for a method 100 of making a wafer in accordance with aspects of the present disclosure. A preparing step 102 prepares an emulsion. An emulsion may be prepared via various methods. For example, an emulsion containing at least one cannabinoid may be made with an emulsifier or ultrasonic liquid processor. In some embodiments, the method includes forming a water-soluble matrix, such as water-soluble cannabinoid nanoparticles or nano emulsions (e.g., approximately 100 nm-300 nm), and an assembly of liposomes are employed to encapsulate the cannabinoid(s). In some embodiments, the water-soluble matrix may comprise primarily of sugar and microcrystalline cellulose.

The emulsion may also contain at least one of cannabinoids, water, dried acacia exudate, birch xylitol, refined coconut oil, MCT oil, *Cannabis* derived terpenes, and botanically derived terpenes. In some embodiments, the emulsion includes NanoStabilizer®-LSO.

A preparing step 104 prepares a spray dry solution. The spray dry solution may be prepared by mixing the emulsion with at least one carbohydrate. For purposes of this disclosure, a carbohydrate may include starch, sugar, fiber, low-calorie sweeteners. For example, the spray dry solution may include a cannabinoid, a starch, and a sugar. In another example, the spray dry solution may include maltodextrin and a sweetener. In another example, the spray dry solution may include cornstarch and sugar.

The amounts of cannabinoid and/or other ingredients incorporated into the spray dry solution may vary. In some example, the amounts may vary depending on the desired final dose.

In some embodiments, concentrations of approximately 10-20 mg of cannabinoids per gram of spray dried cannabinoid and carbohydrate particles are incorporated for a 2.5 mg THC dose.

In some embodiments, concentrations of approximately 15-16 mg cannabinoids per gram of spray dried cannabinoid and carbohydrate particles for a 2.5 mg THC dose.

In some embodiments, concentrations of approximately 25-35 mg of cannabinoids per gram of spray dried cannabinoid and carbohydrate particles for a 5 mg THC dose.

In some embodiments, concentrations of approximately 30-31 mg cannabinoids per gram of spray dried cannabinoid and carbohydrate particles for a 5 mg THC dose.

In some embodiments, concentrations of approximately 55-65 mg of cannabinoids per gram of spray dried cannabinoid and carbohydrate particles for a 10 mg THC dose.

In one example, concentrations of approximately 60-61 mg cannabinoids per gram of spray dried cannabinoid and carbohydrate particles for a 10 mg THC dose.

A spray drying step 106 spray dries the solution into cannabinoid and carbohydrate particles. In one example, the spray drying step includes introducing the spray dry solution to a spray dryer at 125 degrees C. at a rate of 12 mL/min to 16 mL/min into a 2 L spray dryer. In other examples, the temperature setting on the spray dryer and speed of fluid introduced to the spray dryer may be different for larger spray dryers. In other embodiments, other drying techniques may be used. For example, the solution may be dried by freeze drying the solution, or evaporating the solution by heating the solution with a heat source with or without a vacuum oven. In an example, water may be boiled off in the solution and dry cannabinoid containing solute collected.

A preparing step 108 prepares a paste. A paste may be created by mixing various ingredients. In some embodiments, the paste includes the spray dried cannabinoid and carbohydrate (e.g., starch, sugar, etc.) particles. The paste may include salt, baking soda, mint microcrystalline cellulose, vanilla extract, and distilled water. The amounts of spray dried cannabinoid and carbohydrate particles will vary based on the final cannabinoid concentration. For example, the amounts of the spray dried cannabinoid and carbohydrate particles and the sucrose may vary in order to achieve 2.5 mg, 5 mg or 10 mg of THC in the final product.

A preparing step 110 prepares a wafer by heating the paste in a heated vacuum oven. The paste may be measured and spread thin onto parchment paper. The paste may be heated in the oven (e.g., 200°-260° F.) to remove moisture and create a dry cannabinoid infused wafer. In some embodiments, the paste may be heated in an oven at 230° F. In some embodiments, the method includes providing a cannabinoid paste in a heated vacuum oven with an ultimate vacuum measuring 1.0×10-3 Torr, evaporating water out of the paste (e.g., approximately 30-35 minutes), preparing a cannabinoid wafer responsive to evaporating water out of the paste, In some embodiments, the wafer is removed from the oven. The wafer may be cooled. The wafer can be broken down into cannabinoid infused wafer fragments. The measurement of the water activity of the cannabinoid infused wafer fragments may vary. In some embodiments, the water activity measures approximately 0.1-0.65 aw.

FIG. 2 illustrates a flowchart for a method 200 of making a *Cannabis* pouch in accordance with aspects of the present disclosure. A preparing step 202 prepares an emulsion. A preparing step 204 prepares a spray dry solution. A spray drying step 206 spray dries solution into cannabinoid and carbohydrate particles. A preparing step 208 prepares a paste. A preparing step 210 prepares a wafer in a heated vacuum oven. A fragmenting step 212 fragments the wafer into cannabinoid infused wafer fragments. A coating step 214 coats the cannabinoid infused wafer fragments with starch. In some embodiments the step 214 may include coating the cannabinoid infused wafer fragments. A dispensing step 216 dispenses the coated cannabinoid infused wafer fragments into pouches. In some embodiments, the pouches may be labeled.

In one example, the method may include emulsifying THC into a water soluble solution, preparing a maltodextrin, sucralose, and sucrose into a THC water soluble mixture, removing water from the THC water soluble mixture via spray dryer to create a THC, forming a paste by mixing THC with sugar, microcrystalline cellulose, baking soda, natural flavoring, vanilla extract, salt, and water, heating the paste under vacuum until water has been evaporated to create a dry wafer and fragmenting the wafer into cannabinoid infused wafer fragments for use in pouches. In some embodiments, various supplements may be used (e.g., silicon dioxide) instead of or in combination with microcrystalline cellulose.

Figure 3:
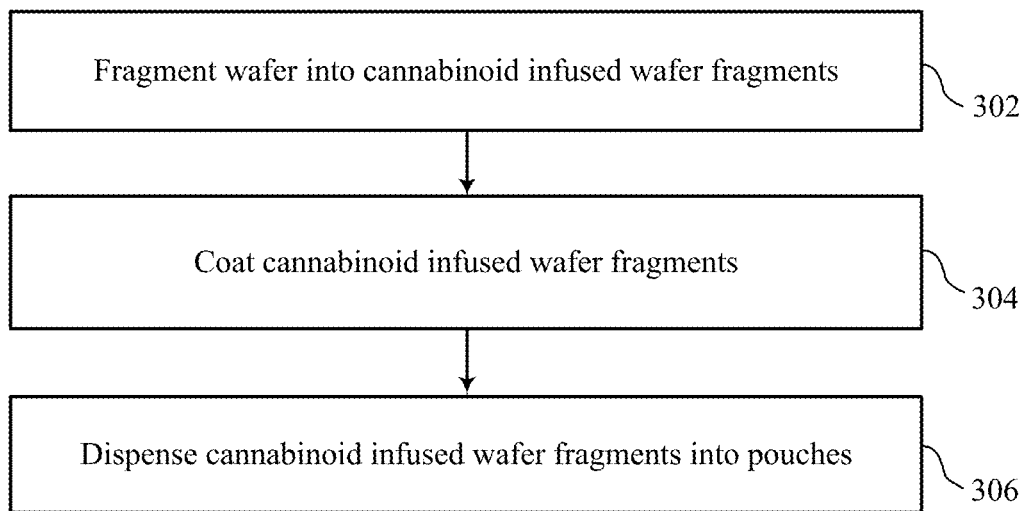
FIG. 3 illustrates a flowchart for a method of making a *Cannabis* pouch in accordance with aspects of the present disclosure.

FIG. 3 illustrates a flowchart for a method 300 of making a *Cannabis* pouch in accordance with aspects of the present disclosure. A fragmenting step 302 fragments a wafer into cannabinoid infused wafer fragments. In some embodiments, the wafer may be broken into cannabinoid infused wafer fragments via other methods.

A coating step 304 coats the cannabinoid infused wafer fragments. In some embodiments, the cannabinoid infused wafer fragments are coated or mixed with starch.

A dispensing step 306 dispenses the coated cannabinoid infused wafer fragments into pouches. As would be understood by one of ordinary skill in the art, after the cannabinoid composition is made, the cannabinoid infused wafer fragments are put into a vertical form fill and seal machine or other machine or process in order to achieve a pouch (e.g., with snus material and a label). For example, the cannabinoid infused wafer fragments may be processed in a vertical form fill and seal machine or other machine or apparatus and using a snus material with the cannabinoid infused wafer fragments. The snus material may comprise of various materials, including water, salt and flavoring. In some embodiments, woven or non-woven material may be used. In some embodiments, fleece may be used.

In some embodiments, the cannabinoid infused wafer fragments are incorporated into pouches by other methods, such as spraying, placing, or otherwise applying the cannabinoid infused wafer fragments onto the pouch material.

The final pouch weight may be of various weights (e.g., approximately between 0.1 g and 0.6 g. The pouches may then be organized into pouches into containers. The containers may be labeled with proper compliance information and trademark(s). The following Example describes a process to illustrate certain aspects of this disclosure, and the Example shall not be construed to limit this disclosure or any patent claim that matures from this disclosure.

Example 1

A 20 L emulsion was prepared containing 300 g of 80% THC distillate (or a combination of THC and other cannabinoids), 18 L of water, 1600 g of NanoStabilizer®-LSO, and 100 g of MCT oil using an Industrial Sono Mechanics BSP-1200® ultrasonic processor.

A spray dry solution was prepared by mixing emulsion with maltodextrin, confectioners sugar, and sucralose to achieve concentrations of 15.178 mg cannabinoids per gram of spray dried cannabinoid and carbohydrate particles for a 2.5 mg dose, 30.356 mg cannabinoids per gram of spray dried cannabinoid and carbohydrate particles for a 5 mg dose, and 60.712 mg cannabinoids per gram of spray dried cannabinoid and carbohydrate particles for a 10 mg dose.

A paste was created by mixing the following ingredients: 1) 56 g of spray dried cannabinoid and carbohydrate particles and approximately 7 g sucrose (confectioners sugar; 2) 1 g salt; 3) 3.2 g baking soda (sodium bicarbonate); 4) 5 g spearmint; 5) 2 g peppermint flavoring powder; 6) 8 g microcrystalline cellulose; 7) 10 g granulated sugar (sucrose); 8) 0.9 g vanilla extract; and 9) 20 g distilled water. The amounts of spray dried cannabinoid and carbohydrate particles and sucrose will vary based on the final cannabinoid concentration (e.g., THC, combination of cannabinoids, etc.). For example, the amounts of spray dried cannabinoid and carbohydrate particles and sucrose will vary in order to achieve 2.5 mg, 5 mg or 10 mg of THC.

The paste was measured in an amount of 112.5 g and spread thinly onto parchment paper. The paste was preheated in an Across International AccuTemp-19 Heated Vacuum oven to 230° F.

A wafer was created by placing 112.5 g of paste on parchment paper into oven and turning on an Agilent IDP-15 scroll pump to achieve a heated vacuum environment of 230 degrees Fahrenheit and a vacuum pressure of −600 in Hg to −700 in Hg for 33 minutes in order to remove moisture and create a dry cannabinoid infused wafer for further processing into cannabinoid infused wafer fragments.

The wafer was removed from the oven and cooled to room temperature. The wafer was ground into cannabinoid infused wafer fragments. The water activity of the cannabinoid infused wafer fragments measured approximately 0.22 aw.

Gluten-free cornstarch was added in an amount of 3 g to the cannabinoid infused wafer fragments. The cannabinoid infused wafer fragments and cornstarch was mixed thoroughly. The cannabinoid infused wafer fragments were put into a vertical form fill and seal machine in order to achieve a THC pouch using 35 mm wide snus material with a THC label. The cannabinoid infused wafer fragments was put into a vertical form fill and seal machine in order to achieve a THC pouch using 35 mm wide snus material with a THC label. The final pouch weight was between 0.25 g and 0.33 g. The pouches were organized into containers. The containers were labeled with proper compliance information and trademarks.

Terminology and Interpretative Conventions

Any methods described in the claims or specification should not be interpreted to require the steps to be performed in a specific order unless stated otherwise. Also, the methods should be interpreted to provide support to perform the recited steps in any order unless stated otherwise.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/of" shall also be interpreted to be inclusive (e.g., "x and/or y" means one or both x or y). In situations where "and/of" or "or" are used as a conjunction for a group of three or more items, the group should be interpreted to include one item alone, all the items together, or any combination or number of the items.

The terms have, having, include, and including should be interpreted to be synonymous with the terms comprise and comprising. The use of these terms should also be understood as disclosing and providing support for narrower alternative embodiments where these terms are replaced by "consisting" or "consisting essentially of."

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100% in either direction and thus provide support for claims that recite such values or any and all ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range (e.g., 15.2).

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The term "pouch" refers to a container formed by a web of a fibrous material enclosing an interior area or cavity. The pouch is pouch designed for administration of an active ingredient in the oral cavity, and thus, adapted for oral use. In some embodiments, the pouch is a saliva permeable pouch. The pouch may be placed in the oral cavity by the user. Saliva then enters into the pouch, and the cannabinoid composition, which is soluble in saliva, starts to dissolve and is transported into the oral cavity and swallowed, where the cannabinoid may be absorbed.

In order to release the cannabinoid composition, the pouch is water-permeable so as to allow saliva from the oral cavity to penetrate the pouch and enter the cavity, where the saliva can come into contact with the one or more cannabinoids, whereby the one or more cannabinoids are released from the oral pouch.

The cannabinoid composition or cannabinoid infused wafer fragments composition is filled into pouches and is maintained in the pouch by a sealing. The pouch is chemically and physically stable, it is pharmaceutically acceptable, it is easy to fill with cannabinoid composition or cannabinoid infused wafer fragments composition and seal, and it provides a semi-permeable membrane layer which prevent the cannabinoid composition or cannabinoid infused wafer fragments composition from leaving the bag, but permits saliva and therein dissolved or sufficiently small-suspended components from the cannabinoid composition or cannabinoid infused wafer fragments composition in the pouch, such as cannabinoids, to pass through said pouch.

The term "cannabinoids" refer to cannabinoids derived from Cannabis plants and synthetic cannabinoids (e.g., cannabidiol, tetrahydrocannabinol, cannabinol, etc.). The present invention contemplates any pharmacologically active agent present in decarboxylated Cannabis plant material that is absorbed as an active ingredient. In an embodiment, the decarboxylated Cannabis plant material comprises at least one pharmacologically active cannabinoid present as an active ingredient. In an embodiment, the at least one pharmacologically active cannabinoid is a psychoactive agent. In an embodiment, the at least one pharmacologically active cannabinoid is a non-psychoactive agent. In an embodiment, the at least one pharmacologically active cannabinoid is tetrahydrocannabinol. As used herein "tetrahydrocannabinol" refers to d9-tetrahydrocannabinol (THC), a decarboxylation product of its inactive precursor d9-tetrahydrocannabinolic acid (THCA; also referred to herein as cannabinolic acid). In an embodiment, the at least one pharmacologically active cannabinoid is an analog or derivative of tetrahydrocannabinol. In an embodiment, the at least one pharmacologically active cannabinoid is cannabidiol. As used herein "cannabidiol" (CBD) refers to the decarboxylation product of its inactive precursor cannabidiolic acid (CDBA). In an embodiment, the at least one pharmacologically active cannabinoid is an analog or derivative of cannabidiol. In an embodiment, the at least one pharmacologically active cannabinoid is cannabigerol. In an embodiment, the at least one pharmacologically active cannabinoid is an analog or derivative of cannabigerol. In an embodiment, the at least one pharmacologically active cannabinoid is cannabigevarin. In an embodiment, the at least one pharmacologically active cannabinoid is an analog or derivative of cannabigevarin. In an embodiment, the at least one pharmacologically active cannabinoid is tetrahydrocannabivarin. In an embodiment, the at least one pharmacologically active cannabinoid is an analog or derivative of tetrahydrocannabivarin. In an embodiment, the at least one pharmacologically active cannabinoid is cannabidivarin. In an embodiment, the at least one pharmacologically active cannabinoid is an analog or derivative of cannabidivarin.

The term "cannabinoid composition" refers to a composition including a cannabinoid. In some embodiments, the cannabinoid composition includes cannabinoid infused wafer fragments.

The term "cannabinoid infused wafer fragments" refers to a particulate material having a relatively small average particle size (e.g., in a range between approximately 0.001 millimeters (1 micrometer)-approximately 4 millimeters (4000 micrometers).

The terms "micellar cannabinoid" and "liposomal cannabinoid" refer to water-soluble forms of cannabinoids that have superior absorption, bioavailability, and efficiency compared to oil-based cannabinoid products. Cannabinoids are fat-soluble or hydrophobic and not naturally water-soluble molecules. The disclosed technology includes the use of liposomes and micelles, nano-sized structures, to encapsulate cannabinoids within a water-soluble structure. The liposomes and micelles have a protective hydrophilic outer layer which delays the metabolism of cannabinoids in the digestive system. The liposomes may deliver the cannabinoids by fusing to a cell surface or the can swallow the liposome through endocytosis. This delivery to cell walls allows the cannabinoids to bypass metabolism in the gastrointestinal tract. The micelles are smaller and help mix the cannabinoids into hydrophilic body fluids.

The subject matter recited in the claims is not coextensive with and should not be interpreted to be coextensive with any embodiment, feature, or combination of features described or illustrated in this document. This is true even if only a single embodiment of the feature or combination of features is illustrated and described in this document.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed:

1. A method of making an oral product comprising:
preparing an emulsion with at least one cannabinoid and at least one carbohydrate particle;
preparing a spray dry solution with the emulsion;
spray drying the solution into cannabinoid and carbohydrate particles;
preparing a paste with the cannabinoid and carbohydrate particles;
heating the paste in a heated vacuum oven for less than 1 hour at a temperature of 200° F.-260° F. to evaporate water from the paste;
preparing a wafer responsive to evaporating water from the paste;
fragmenting the wafer into cannabinoid infused wafer fragments;
coating the cannabinoid infused wafer fragments in starch;
and
dispensing the cannabinoid infused wafer fragments into a pouch.

2. The method of claim 1, wherein the emulsion includes cannabinoid nanoparticles.

3. The method of claim 2, wherein the cannabinoid nanoparticles are approximately 100 nm-300 nm in size.

4. The method of claim 1, wherein the emulsion includes at least one of micellar cannabinoid nanoparticles and liposomal cannabinoid nanoparticles.

5. The method of claim 1, wherein the paste further includes at least one of sucrose, maltodextrin, microcrystalline cellulose, modified food starch, sodium bicarbonate, natural flavoring, botanically derived terpenes, *Cannabis* derived terpenes, vanilla extract, sodium chloride, distilled water, and sucralose.

6. The method of claim 1, further comprising:
labeling the pouch.

7. The method of claim 1, wherein the water activity of the cannabinoid infused wafer fragments is approximately 0.1-0.65 aw.

8. A method of making a wafer comprising:
preparing an emulsion;
preparing a spray dry solution;
spray drying the solution into particles;
preparing a paste;
heating the paste in a heated vacuum oven for less than 1 hour at a temperature of 200° F.-260° F. to evaporate water out of the paste;
and
preparing a wafer responsive to evaporating water out of the paste.

9. The method of claim 8, wherein the emulsion includes cannabinoid nanoparticles.

10. The method of claim 9, wherein cannabinoid nanoparticles are approximately 100 nm-300 nm in size.

11. The method of claim 8, wherein the emulsion includes at least one of micellar cannabinoid nanoparticles and liposomal cannabinoid nanoparticles.

* * * * *